(12) United States Patent
Zeitsch et al.

(10) Patent No.: US 6,642,396 B1
(45) Date of Patent: Nov. 4, 2003

(54) PROCESS FOR THE PRODUCTION OF FURFURAL FROM LIGNOSULPHONATE WASTE LIQUOR

(75) Inventors: Karl J. Zeitsch, deceased, late of Zwa Zulu Natal (ZA); by Philipp Daniel Steiner, legal representative, Kloof (ZA)

(73) Assignee: International Furan Technology (PTY) Limited, Durban (ZA)

( * ) Notice: Subject to any disclaimer, the term of this patent is extended or adjusted under 35 U.S.C. 154(b) by 0 days.

(21) Appl. No.: 09/958,936

(22) PCT Filed: Apr. 14, 2000

(86) PCT No.: PCT/ZA00/00072

§ 371 (c)(1),
(2), (4) Date: Jan. 14, 2002

(87) PCT Pub. No.: WO00/63488

PCT Pub. Date: Oct. 26, 2000

(30) Foreign Application Priority Data

Apr. 16, 1999 (DE) .......................................... 199 17 178

(51) Int. Cl.[7] .............................................. C07D 307/50
(52) U.S. Cl. ........................ 549/489; 422/197; 422/198
(58) Field of Search .......................... 549/489; 422/197, 422/198

(56) References Cited

U.S. PATENT DOCUMENTS

| 1,838,109 A | 12/1931 | Richter |
| 2,845,441 A | 7/1958 | Morse et al. ............. 260/347.9 |
| 4,401,514 A | 8/1983 | Kanzler et al. ................ 203/15 |
| 4,533,743 A | 8/1985 | Medeiros et al. ........... 549/489 |

FOREIGN PATENT DOCUMENTS

| EP | 0 124 507 A1 | 11/1984 |
| FR | 1.129.139 | 1/1957 |

*Primary Examiner*—Amelia Owens
(74) *Attorney, Agent, or Firm*—Young & Thompson

(57) ABSTRACT

A process for the production of furfural from lignosulphonate waste liquor which contains pentose is described, the process essentially comprising the maintenance of a boiling condition of the liquor at predetermined pressures for a sufficient time to convert the pentose to furfural and for the furfural produced to be removed without reacting with pentose, lignosulphonate or itself. Hot air or some other gas under pressure or hot mercury may be used to maintain the boiling of the liquor to ensure that the furfural produced transfers from the liquid to the gas phase and is transported from the reactor in the gas stream. Apparatus for carrying out the process includes a columnar reactor (4) with means (8) to control the pressure, an inlet for preheated liquor, an inlet for hot air under pressure at a low level, an outlet for spent liquor and an outlet for the gaseous phase, from which the furfural is recovered.

11 Claims, 1 Drawing Sheet

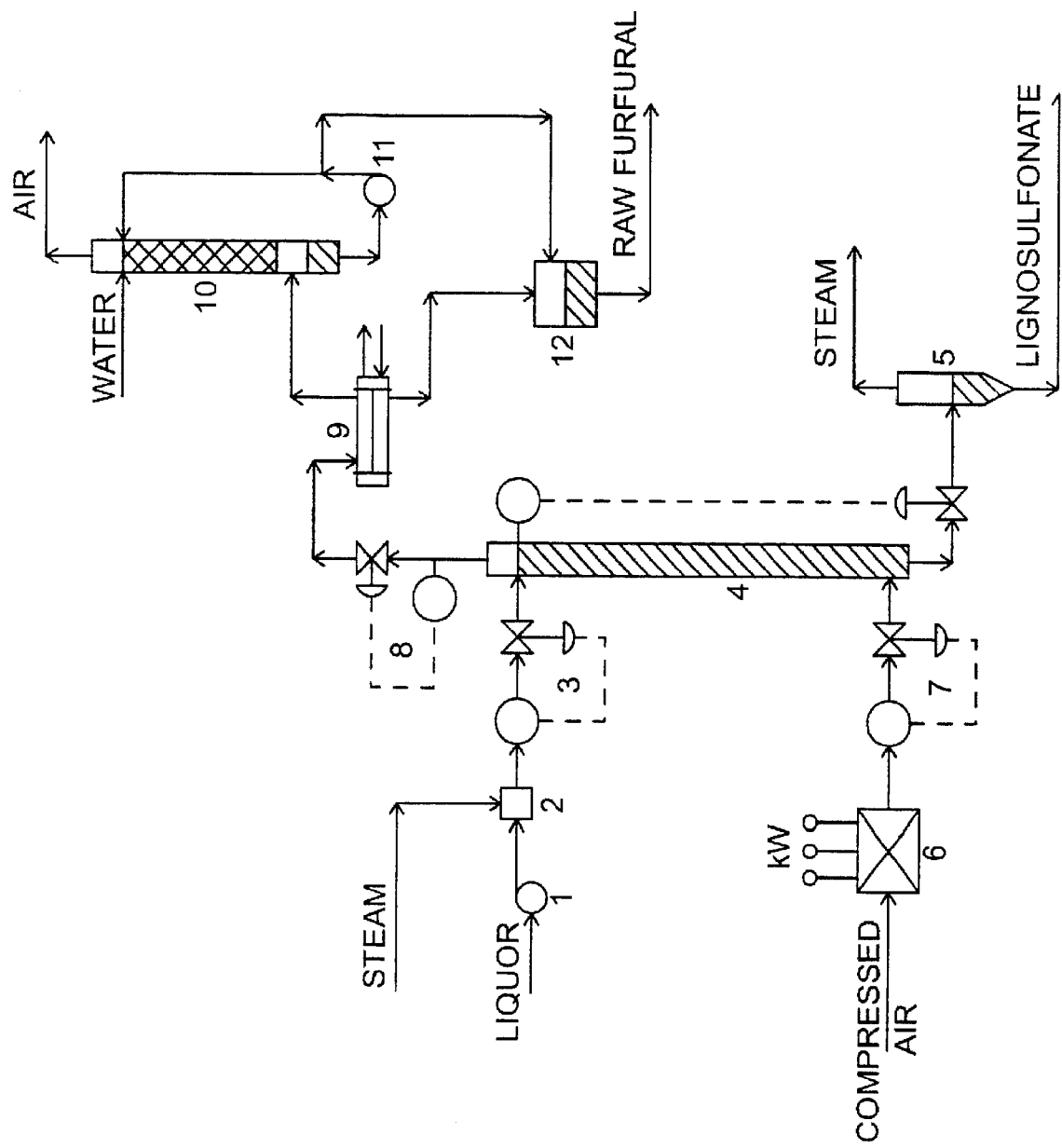

PROCESS FOR THE PRODUCTION OF FURFURAL FROM LIGNOSULPHONATE WASTE LIQUOR

TECHNICAL FIELD OF THE INVENTION

This invention relates to the production of furfural from lignosulphonate waste liquor.

BACKGROUND OF THE INVENTION

Depending on the particular wood processed, the sulphite pulping process results in a waste liquor which may contain from 0.9 to 5.6 percent of pentose which makes it a candidate for the production of furfural.

Conventionally, the waste liquor is thickened to a solids content of 50 percent or totally dried, the liquor or solid being sold as lignosulphonate. Pentose is an undesirable constituent of this liquor.

The waste liquor from the process is saturated with calcium sulphate, so that the high temperature required for furfural production (preferably above 200 degrees Centigrade) results in the rapid and severe deposition of calcium sulphate on the heated surfaces, which renders extended continuous operation impossible.

If heat exchangers are avoided by substitution of direct steam injection, it is not possible thermodynamically to keep the liquor in a state of boiling during its residence time because the substances in solution elevate the boiling point Thus, at any pressure, the boiling point of the liquor is higher than the condensation point of steam. Consequently, the furfural produced from the pentose remains temporarily dissolved in the liquid phase where, under the catalytic effect of the liquor's innate acidity, the furfural can react with pentose, or the lignosulphonate, and with itself, thus incurring great losses and consequent poor yields.

It is an object of the present invention to provide a process for the efficient production of furfural from lignosulphonate liquors as well as apparatus for carrying out the process.

DISCLOSURE OF THE INVENTION

According to the invention a process for the production of furfural from lignosulphonate waste liquor containing pentose is characterised by maintaining the liquor at boiling point by controlled decompression for a time sufficient for the pentose to be converted to furfural and to be removed in the vapor substantially without reacting with pentose, lignosulphonate or itself.

The reactor may be a batch or continuous reactor.

In a preferred form batch process, a lignosulphonate liquor is heated by steam, in a reactor which is continuously depressurised to pressures which are sufficient to maintain boiling of the liquor, the furfural formed migrating to the vapor phase and is discharged with the condensate and recovered.

In a continuous process according to the invention, the liquor is boiled in a continuous reactor by means of an auxiliary heat source, the liquor being discharged while the furfural formed is substantially instantaneously and completely transferred into the gas phase leaving the reactor and from which it is separated.

In a form of the invention the liquor is heated in the reactor by means of an auxiliary beat source, the liquor being discharged while the furfural formed is substantially instantaneously and completely transferred into the gas phase from which it separated.

The auxiliary heat source is preferably heated air under pressure and this may be introduced at a low level in the reactor. The air percolates through the liquor in the reactor, and by giving up its heat it maintains the liquor in a state of boiling before leaving the reactor.

The liquor is preferably introduced into the reactor at a temperature of between 180 and 280 degrees Centigrade.

A control circuit may be provided to maintain the pressure in the head of the reactor at a value slightly below the pressure of the entering liquor. In this way the resulting liberating steam causes the liquor to undergo a minor depression to a lower temperature which forces the furfural to the vapor phase, while the heated air maintains a state of boiling of the liquor throughout the entire reactor. Thus, the furfural produced from the pentose is immediately and completely vapourised as it is formed; and joins the air and some vapourised water to form a gaseous mixture with minimum yield loss of furfural, because reactions between furfural and pentose on the one hand, and with the lignosulphonate on the other hand cannot take place because the pentose and lignosulphonate remain in solution. The reaction of furfural with itself is prevented by the absence of hydrogen ions in the vapour phase.

The residence time in the reactor is chosen for there to be complete conversion of the pentose. No addition of acid is required because of the innate acidity of the liquor which effects a sufficiently strong catalysis.

No heat exchangers are required, thereby avoiding the problems associated with calcium sulphate as discussed above.

Instead of using heated air as the auxiliary heat source, other suitable heated gases or gas mixtures (such as hot combustion gas) or hot mercury may be used, all of which are readily separated from the liquor at the end of the reaction.

It will be appreciated that the heat required by the auxiliary heat agent is relatively small, as in essence all that is required of it is to vapourise the furfural produced. The low heat of vapourisation of furfural, especially at high temperatures, ensures a low auxiliary heat requirement.

The yield of furfural increases with the increasing temperature in the reactor as the losses due to reactions with pentose and lignosulphonate as well as bisulphites are suppressed at higher temperatures on account of the entropy effect on all aggregation reactions.

It will be appreciated that it is not necessary to add any acid to the liquor for catalysis, as the innate acidity of the liquor effects a sufficiently strong catalysis.

DESCRIPTION OF THE INVENTION

The process of the invention is described below with reference to the accompanying flow diagram.

A pump 1 feeds a lignosulphonate waste liquor through an in-line mixer 2, where steam injection heats it to a temperature of between 180 and 280 degrees Centigrade, thus raising the pressure accordingly. By means of a throttle valve 3, the liquor is submitted to a minor pressure reduction in the head of a thermally insulated columnar reactor 4 and then flows downwardly to leave at the bottom via a cyclone 5 which results in decompression, cooling and thickening.

Compressed air is heated electrically in a heat exchanger and this is fed via control circuit 7 into the bottom of the reactor. The hot air percolates upwardly, giving up its heat to the liquor and thereby maintaining the liquor in a state of ebullition before leaving the head of the reactor via a control circuit 8, a condenser 9, and an atmospheric absorption column 10 equipped with a circulation pump 11.

The control circuit maintains the pressure in the head of the reactor at a value slightly below the pressure of the entering liquor, so that in liberating steam the liquor undergoes a minor depression to a somewhat lower temperature while the hot air introduced at the bottom ensures continuous boiling of the liquor throughout the reactor. The furfural formed is instantaneously and completely vapourised and joins the air and vapour to form a gaseous mixture which is condensed in 9 then collected in tank 12. Small quantities of furfural entrained by air are recovered in the absorption column and collected in tank 12.

The input rate of the liquor and the dimensions of the reactor are chosen to match a predetermined residence time of the liquor in the reactor.

What is claimed is:

1. A process for the production of furfural form lignosulphonate waste liquor containing pentose characterised in that the liquor is maintained at boiling point by means of an auxiliary heat source for a sufficient time for the pentose to be completely converted to furfural which is immediately transferred-to the vapour phase as it is formed; and separating the vapour phase from the liquid phase.

2. The process according to claim 1 characterised in that the auxiliary heat source is heated air under pressure which is introduced at a low level in the reactor, the rate of introduction and the temperature being predetermined for it to give up its heat during percolation through the liquor to maintain the liquor in a state of boiling.

3. A reactor for carrying out the process of claim 1 characterised in that it comprises a columnar cylinder having an inlet for preheated lignosulphonate waste liquor, means to control the pressure at last in the head of the reactor, an outlet for furfural-stripped liquor at a low level, an inlet for heated auxiliary matter which is readily separable from the liquor, such inlet being at a low level when the auxiliary matter is lighter than the liquor, and an outlet at a high level for the vapour phase.

4. A reactor according to claim 3 characterised in that the outlet for the gas phase includes a condenser.

5. A reactor according to claim 3 characterised in that the heated auxiliary matter is preheated air under pressure.

6. A reactor according to claim 3 characterised in that a control circuit is provided which is adapted to maintain the pressure in the head of the reactor at a value slightly below the pressure of the liquor so that in liberating steam the liquor undergoes a minor depression in temperature while the hot auxiliary matter ensures maintenance of continuous boiling of the liquor throughout the reactor.

7. A process according toe claim 1 characterised in that the partial decompression in the reactor leads to a temperature between 170 and 270 degrees Centigrade.

8. A process according to claim 1 characterised in that the auxiliary agent is hot combustion gas.

9. A process according to claim 1 characterised in that the auxiliary agent is an advantageous gas mixture.

10. A process according to claim 1 characterised in that the auxiliary agent is hot liquid mercury which is introduced at a high level.

11. A process according to claim 1 characterised in that the gas used as auxiliary gas is used at a temperature between 400 and 2000 degrees Centigrade and preferably between 600 and 2000 degrees Centigrade.

* * * * *